United States Patent [19]

Johnson

[11] Patent Number: 5,166,063
[45] Date of Patent: Nov. 24, 1992

[54] IMMOBOLIZATION OF BIOMOLECULES BY ENHANCED ELECTROPHORETIC PRECIPITATION

[75] Inventor: Kirk W. Johnson, Indianapolis, Ind.

[73] Assignee: Eli Lilly and Company, Indianapolis, Ind.

[21] Appl. No.: 546,101

[22] Filed: Jun. 29, 1990

[51] Int. Cl.$^5$ .................. C25D 13/00; C12N 13/00; C12M 1/40
[52] U.S. Cl. .......................... 435/173; 435/288; 435/291; 435/817; 204/180.2; 204/403; 205/80; 205/83
[58] Field of Search .............. 435/288, 291, 817, 173; 204/403, 14.1, 180.2, 15, 181.1; 205/83, 80

[56] References Cited

U.S. PATENT DOCUMENTS

| | | | |
|---|---|---|---|
| 3,758,396 | 8/1971 | Vieth et al. | |
| 3,839,175 | 10/1974 | Keyes | |
| 4,120,759 | 10/1978 | Asami et al. | 204/14.1 |
| 4,242,096 | 12/1980 | Oliveira et al. | 436/500 |
| 4,245,005 | 1/1981 | Regnier et al. | |
| 4,940,516 | 7/1990 | Wegmann et al. | 204/14.1 |
| 4,999,091 | 3/1991 | Doroszkowski et al | 204/14.1 |

FOREIGN PATENT DOCUMENTS 8807192 9/1988 World Int. Prop. O.
8807193 9/9188 World Int. Prop. O.

OTHER PUBLICATIONS

Aizawa et al., J. Chem. Soc. Japan, Nihon Kagaku Kaishi, 11, pp. 2210-2213 (1987).
Aizawa et al., "Molecular Films in Biosensors", VTT Symposium (1988).
Ikariyama et al., J. Electrochem. Soc., 136(3), 702 (1989).
Ikariyama et al., Anal. Let., 20(9), 1407 (1987).
Kimura et al., J. Electrochem. Soc., 136(6), 1744 (1989).
Suzucs et al., J. Electrochem. Soc., 136(12), 3748 (1989).
Tamiya et al., Sensors and Actuators, 18, 297 (1989).
Coury et al., "Electrochemical Sensors Based on Polymer Films Immobilized Gamma Irradiation", Chap. 5, Chemical Sensors and Micro Instrumentation (1989).

Primary Examiner—James C. Housel
Assistant Examiner—Will Chan
Attorney, Agent, or Firm—Douglas J. Taylor; Leroy Whitaker

[57] ABSTRACT

The present invention provides a method for immobilizing biomolecules on a conductive substrate to produce a biosensor.

8 Claims, 1 Drawing Sheet

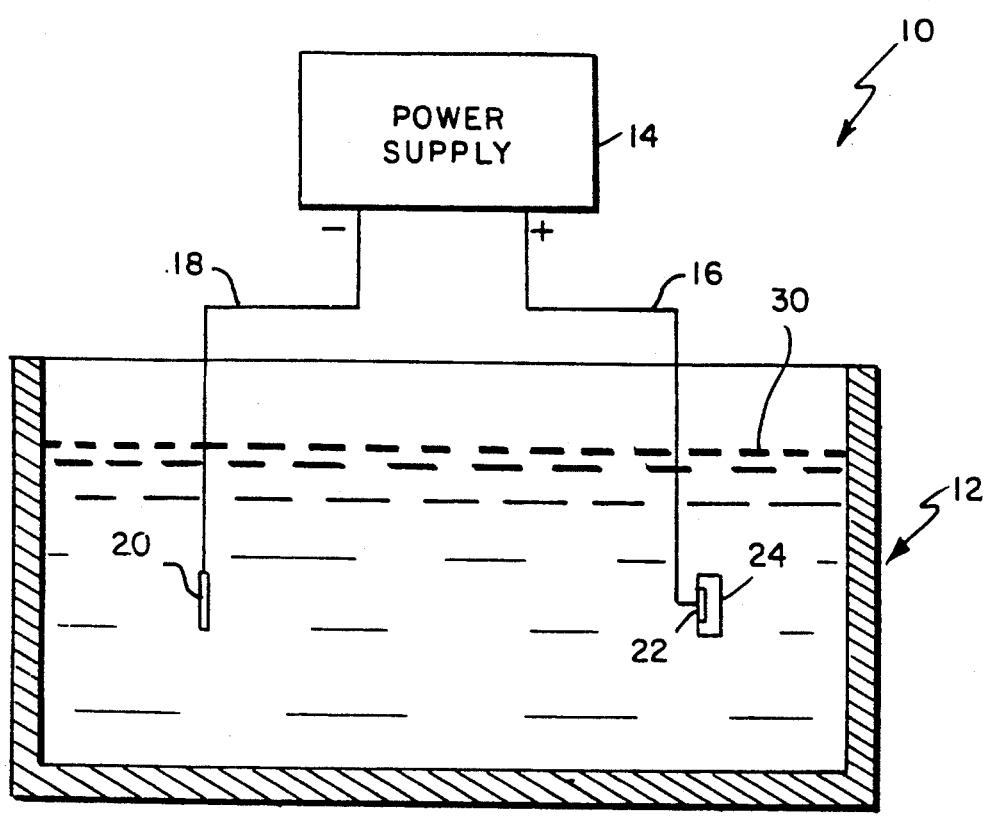

IMMOBOLIZATION OF BIOMOLECULES BY ENHANCED ELECTROPHORETIC PRECIPITATION

BACKGROUND OF THE INVENTION

The present invention relates to a method for immobilizing biomolecules on a conductive substrate. More particularly, this invention relates to a method for electrodepositing biomolecules such as enzymes and antibodies onto the conductive substrate followed by chemical crosslinking of the biomolecules to form a water insoluble mass.

Immobilization of biomolecules on a substrate is necessary for many commonly employed analytical or industrial applications utilizing biomolecules. Immobilization converts typically water soluble biomolecules such as enzymes or antibodies into water insoluble complexes through attachment of at least some of the molecules to a water insoluble physical support material. Biomolecules so immobilized can often be used in many applications without change in their concentration or activity over time. Immobilization has an additional advantage in that biomolecules can be retained only in specific desired regions of an apparatus or sensor, minimizing material costs and maximizing detectable bioactivity.

An important analytical use of immobilized biomolecules such as enzymes, antibodies, or glycoproteins such as lectins is in biosensors that detect the presence or concentration of selected physiological molecules as a result of the interaction of the physiological ligand with the immobilized biomolecules. Unfortunately, adapting known immobilization techniques for use in conjunction with the miniature electrochemical biosensors fabricated using conventional semiconductor manufacturing techniques can be difficult. Current semiconductor techniques allow fabrication of a sensor with a surface area of as little as 1.0 $\mu m^2$. This small areal dimension presents difficulties in sensor construction since the fabrication of biosensors generally requires deposition of a biomolecule only on the surface of the working electrode, which is used to monitor a product of the enzymatic reaction. Biomolecules deposited on other areas of the biosensor would react to produce a product that could not be detected, wasting the often costly biomolecule.

One method of overcoming problems in depositing biomolecules relies on electrophoresis to promote migration of charged biomolecules such as proteins, amphipathic lipids, or nucleic acids. In the appropriate medium, such biomolecules contain positively or negatively charged moieties that are attracted to an opposing pole of a generated electric field. Migration of the biomolecule contained within the medium toward and deposition on an electrode having a polarity opposite that of the charged molecule is therefore promoted if a potential across two electrodes in a medium is created.

For example, electrophoretic deposition techniques were utilized by Ikariyama et al., *J. Electrochem, Soc.*, 136(3), pp. 702–706 (1989). This method promoted the codeposition of platinum particles and the enzyme glucose oxidase. At the pH where platinization normally takes place (pH=3.5), the glucose oxidase has a net positive charge since the pH is lower than its isoelectric point of 4.3. The glucose oxidase is therefore attracted to an oppositely charged electrode along with the platinum ions. To enhance the stability of the deposited enzyme, the sensor is dipped into solutions of albumin and glutaraldehyde to cross-link the molecules. However, this technique can result in the inactivation of the enzyme because of the relatively low pH employed to promote codeposition of enzyme.

Aizawa et al., *J. Chem. Soc. Japan (Nippon Kagaku Kaishi)*, 11, pp. 2210-2213 (1987) have reported the development of a technique for electrodepositing glucose oxidase. The glucose oxidase was absorbed on a platinum electrode surface at a controlled potential from an aqueous solution. The optimal conditions for their deposition were 0.1 V vs. Ag/AgCl and pH 3. The maximum thickness achieved by this method was four molecule thick layers of glucose oxidase, equivalent to approximately $56 \times 10^{-9}$m maximum glucose oxidase film thickness. The technique was evaluated at pH values ranging from 3 to 9 resulting in the optimal deposition at a pH of 3. The extremely thin layer deposited by this technique is inadequate for many Purposes that require that the interaction of the ligand with the biomolecule be a non-rate limited factor in the reaction. A further disadvantage is the limited lifetime and reusability of such thin layers of immobilized molecules.

Accordingly, it is an object of this invention to provide a method for depositing and immobilizing a relatively thick layer of molecules biomolecules on a conductive substrate so that the interaction of a ligand with a biomolecule is not rate-limited.

It is another object of this invention to provide a method for reproducibly and accurately depositing and immobilizing biomolecules onto miniature electronic sensors.

A further object of this invention is to provide a method for simultaneously depositing and immobilizing a plurality of different biomolecules onto a conductive substrate.

An additional object of this invention is to provide a method for depositing and immobilizing biomolecules in a manner resulting in layers with thicknesses ranging from $10^{-8}$ to $10^{-5}$ m.

Accordingly, a method for preparing a biosensor electrode having a conductive substrate coated with a desired biomolecular species includes preparing a solution of at least one species of biomolecule intended for deposition buffered within a range sufficient to prevent denaturization of the biomolecules, and to a value such that all species of biomolecules intended for deposition have the same net electric charge sign due to their respective isoelectric points. The biosensor electrode and a counter electrode are immersed in the solution, and a potential difference of between about 100 millivolts and 1 volt is created between the electrodes, causing a current to flow. The potential is varied with time in a manner calculated to cause the current flow between the electrodes to remain substantially constant, inducing migration toward and subsequent deposition on the biosensor electrode. After a desired thickness of the biomolecule has been deposited on the biosensor electrode, the stability of the deposited biomolecular film can be enhanced by crosslinking with a suitable crosslinking agent.

In preferred embodiments the solution containing a biomolecule is aqueous, and the current between the biosensor electrode and the counter electrode is selected to be about 5 mA/cm$^2$. The voltage is adjusted upward over the course of the deposition process to maintain a constant current despite the increasing electrical resistance of the biosensor electrode due to biomolecular film deposition. Deposition continues until an average film thickness over the biosensor electrode is greater than 5 micrometers.

One advantage of the present invention is its wide applicability to conductive substrates having differing geometries. Because biomolecule deposition is electrophoretically based, biomolecules can be deposited on virtually any conductor or semiconductor independent of shape or topography. For instance, a very rough conductor surface may be uniformly covered with a biomolecular film or the inside of a conductive material such as platinum tubing could be coated with a biomolecule very easily and inserted into a flowing stream system for analytical purpose. Also, in contrast to many other film deposition techniques, the deposition of the biomolecules is localized in such electrophoretic techniques, with the desired biomolecule only being deposited in the vicinity of the conductive substrate.

Another advantage lies in the relatively thick layers of biomolecules which can be deposited on a biosensor electrode. Many physiologic applications involve interaction between relatively large amounts of a particular physiologic ligand to be detected and a biomolecule deposited on a biosensor electrode. Very thin monomolecular films or films having a thickness much less than 1 micrometer may cause the reaction between the physiologic ligand and the biomolecule to be rate limited due to the small amounts of biomolecule available for reaction, decreasing the sensitivity of the sensor and providing a non-linear interaction function (between the biomolecule and the ligand) that could make determination of the amount of ligand present in a solution difficult.

Another advantageous feature of the present invention results from the application of a constant current over the course of the deposition on the biosensor electrode. This results in a steady deposition of the biomolecule on the biosensor electrode even though biomolecule deposition blocks the electrode surface and ultimately increases electrical resistance. Because the resistance of the biosensor electrode increases over the course of the deposition process, both the current and the rate of biomolecule deposition ordinarily decreases unless the voltage is not gradually increased. This decrease in deposition rate would continue until no further deposition occurs, even though the deposited film may be much less thick than required. In contrast, the present invention holds the current constant and allows the voltage to increase as resistance increases, until the voltage approaches a value at which water will be either reduced or oxidized to form gas bubbles, thereby promoting formation of films having a thickness greater than 10 micrometers.

Another advantage of the present invention is its utility at pH values comparable to the physiologic pH values at which a biomolecule is formed. Very thick films of proteinaceous biomolecules such as enzymes can be deposited at physiologic pH (7.4) in aqueous solutions, minimizing potential problems with inactivation or denaturation of the enzyme that can be encountered with other methods of depositing enzyme films.

Additional features and advantages of the invention will become apparent to those skilled in the art upon consideration of the following detailed description of preferred embodiments exemplifying the best mode of carrying out the invention as presently perceived.

BRIEF DESCRIPTION OF THE FIGURE

FIG. 1 is a schematic illustration of an apparatus for electrodeposition of biomolecules onto a biosensor electrode submerged in an aqueous fluid containing a desired biomolecule.

DESCRIPTION OF THE PREFERRED EMBODIMENTS

As shown in FIG. 1, an electrodeposition apparatus 10 is suitable for implementing the process of the present invention. The apparatus 10 includes a container 12 configured to hold a liquid 30. The liquid 30 can be either a solution or suspension containing a desired species of biomolecule. An electrical power supply 14 having a positive lead 16 connected to biosensor electrode 22 and a negative lead 18 connected to a counter electrode 20 is provided to supply substantially constant current flow between the two electrodes 20 and 22. The biosensor electrode 22 forms a portion of a biosensor unit that includes the biosensor electrode 22 and an electrically non-conductive substrate 24. The leads 16 and 18 are electrically shielded with a nonconductive material capable of withstanding immersion in the liquid 30.

The direction of current flow can be reversed if desired by switching the connections of leads 16 and 18 to the power supply 14 to make lead 16 negatively charged and lead 18 positively charged. Since both the leads 16 and 18 are shielded, and the substrate 24 surrounding the biosensor electrode is constructed from a non-conductive material, deposition of biomolecular species contained in liquid 30 only occurs on the electrode 20 or 22 charged in the opposite sense to the charge of the biomolecule in the liquid 30.

Biomolecules suitable for deposition on electrodes 20 or 22 include but are not limited to the following classes of naturally occurring or artificially synthesized molecules or molecular groupings that can exist as components of biological systems: peptides, oligopeptides, proteins, apoproteins, glycoproteins, antigens and antibodies thereto, antibody fragments, haptens and antibodies thereto, receptors and other membrane proteins, protein analogs in which at least one non-peptide linkage replaces a peptide linkage, enzymes and enzyme precursors, coenzymes, enzyme inhibitors, amino acids and their derivatives, hormones, lipids, phospholipids, glycolipids, liposomes, nucleotides, oligonucleotides, polynucleotides, and their art-recognized and biologically functional analogs and derivatives including, for example; methylated polynucleotides and nucleotide analogs having phosphorothioate linkages; plasmids, cosmids, artificial chromosomes, other nucleic acid vectors; antisense polynucleotides including those substantially complementary to at least one endogenous nucleic acid or those having sequences with a sense opposed to at least portions of selected viral or retroviral genomes, and any other biologically active molecule. Any of the preceding biomolecules having weak or non-existent polarity or induceable polarity under the conditions prevailing in apparatus 10 can be covalently linked to an appropriate charged carrier to form a charged complex that can be deposited on the electrodes 20 or 22.

Members of the preceding classes of biomolecules and any combination of specific members thereof can be placed in solution or in suspension as colloidal particles in the liquid 30 using art recognized techniques that depend on the composition of liquid 30. Generally, liquid 30 is an aqueous solution, such as physiological saline, capable of conducting a substantial electrical current. Other additives, such as non-ionic surfactants and anti-foaming agents can also be added to the solution as desired.

The direction, rate of migration, and rate of deposition of biomolecules originally in solution or suspended in liquid 30 onto the electrodes 20 and 22 can be controlled with great sensitivity by appropriately adjusting the pH of the liquid 30. This control is based upon use of conventional electrophoretic techniques applicable to permanently charged moieties that give the biomolecule a net charge in the liquid 30 depending on the pH of the liquid 30. The pH at which a molecule has zero net negative charge, and thus will not migrate under the influence of an electric field, is defined as its isoelectric point. At pH values greater than the isoelectric point, the molecule has a net negative charge; conversely at pH values less than the isoelectric point, the molecule has a net positive charge. Accordingly, in the apparatus shown in the Figure, the pH of the liquid 30 is adjusted to greater than or less than the isoelectric point of the desired biomolecule to be deposited on the electrodes 20 or 22. This adjustment can be accomplished using known acids or alkaline agents as desired.

Crosslinking agents, either introduced to the solution contemporaneus with introduction of the desired biomolecule, or introduced after deposition on the electrodes 20 and 22, are useful for promoting formation of an essentially water insoluble deposited mass on the electrodes. Crosslinking agents generally include polyfunctional bridging groups capable of covalently binding with the desired biomolecule, but can also include radiation or other agents that act to promote covalent binding between biomolecules without bridging groups. The type of crosslinking agent employed will vary according the particular biomolecules deposited, but can include for example silane agents, alkylamine coupling agents, isothiocyanate coupling agents, triazine coupling agents, azo coupling agents, phenylhydrazine coupling agents, carbodiimide coupling agents, and acid chloride coupling agents. The use of glutaraldehyde is of particular utility in the present invention, although other chemical coupling agents such as '4-azidophenacyl bromide, benzophenone-3,3',4,4'-tetracarboxylic dianhydride, biotin N-hydroxysuccinimide ester, biotin 4-nitrophenyl ester, 2,2'-biquinolone-4,4'-dicarboxylic acid, bis(4-fluoro-3-nitrophenyl)sulfone, 1,5-bis(succinimidooxycarbonyloxy)pentane, 4-(BOC-aminomethyl)phenylisothiocyanate, N-BOC-1,6-diamino-hexane hydrochloride, bromopyruvic acid, cyanuric chloride, 4,4'-diazidostilbene-2,2'-disulfonic acid disodium salt, diethylenetriamine pentaacetic acid dianhydride, diethylene pyrocarbonate, 1,5-difluoro-2,4-dinitrobenzene, 1,6-diisocyanohexane, 4,4'-diisothiocyanatostilbene-2,2'-disulfonic acid disodium salt, dimethyl adipimidate dihydrochloride, N-(dimethylaminopropyl)-N'-ethylcarbodiimide hydrochloride, dimethyl 3,3'-dithiodipropionimidate dihydrochloride, dimethylpimelinediimidate dihydrochloride, dimethyl suberimidate dihydrochloride, 3,3'-dithiodipropionic acid bis(N-hydroxysuccinimide ester), 4-fluoro-3-nitrophenyl azide, formaldehyde, fumaronitrile, glutaraldehyde, glutaronitrile, glycolaldehyde, hexamethylene diisocyanate, 6-hydroxy-2-naphthyl disulfide, 3-(4-hydroxyphenyl)propionic acid N-hydroxysuccinimidester, 2-iminothiolane hydrochloride, 4-maleimidobutyramidomethyl-polystyrene, N,N'-(1,4-phenylene)dimaleimide, polyethylene glycol 600 diacid, N-succinimidyl-3-(2-pyridylthio)propionate, N-succinimidyl 3-maleimidobenzoate, N-succinimidyl 4-maleimidobutyrate, N-succinimidyl 6-maleimidocaproate, N-succinimidyl 3-maleimidopropionate, thiodiethyleneglycol, toluylene-2,4-diisocyanate, and m-xylylene diisocyanate can also be used as bivalent crosslinking agents.

Biosensor electrodes produced according to the method of the invention can be used in a wide variety of molecular detection systems, including amperometric electrochemical biosensors, calorimetric, acoustic, potentiometric, optical, and ISFET based biosensors.

To better appreciate certain features of the invention, the following Examples are presented

EXAMPLE 1

A 5% by weight solution of glucose oxidase is prepared utilizing a phosphate buffered saline solution (pH 7.4) as the solvent. Glucose oxidase is carefully dissolved in the saline solution by slow stirring, being careful while stirring to prevent foaming of the solution which could result in denaturation of the glucose oxidase. An electrodeposition cell is filled with this solution and the biosensor electrode on which the enzyme is to be deposited, along with a counter electrode, are submerged inside the cell. Electrical connections are made to a galvanostat and current is maintained at a constant density of 5 mA/cm$^2$ on the electrode surface. The current flow is oriented in a direction that results in a positive net charge on the electrode surface to attract the negatively charged glucose oxidase molecules. The current is applied for 2 minutes. Throughout the course of the deposition, the voltage applied does not exceed 0.5 Volts. The electrode is then removed from the enzyme solution and submerged in deionized, distilled water with no agitation for 5 seconds to remove residual glucose oxidase.

The electrode is then submerged in a solution containing 2.5% by volume glutaraldehyde in phosphate buffered saline (pH 7.4) for 30 minutes to covalently crosslink the glucose molecules together and form a water-insoluble mass. The electrode is again submerged in deionized, distilled water for 5 seconds and allowed to dry in air for 30 minutes.

Inspection of the electrode reveals that the glucose oxidase layer is approximately 1.5 $\mu$m thick when dry. In subsequent testing it was observed that the glutaraldehyde crosslinking is effective to prevent the glucose oxidase from going back into solution. The enzymatic component of the biosensor is observed to be functional at this point.

EXAMPLE 2

Codeposition of two or more biomolecules on an electrode surface is also possible providing their isoelectric points are all either higher or lower than the pH of the deposition solution. In this example a phosphate buffered saline solution (pH 7.4) containing 5% by weight glucose oxidase and 5% by weight albumin is prepared. The glucose oxidase and albumin have isoelectric point values of 4.3 and 4.7 respectively, resulting in both molecules possessing a negative charge in the pH 7.4 solution. A current density of 5 mA/cm$^2$ is applied to the electrode for 2 minutes while submerged in the glucose oxidase/albumin solution. The molecules are crosslinked in the glutaraldehyde solution as described in Example 1, rinsed, and dried. The resulting glucose oxidase/albumin layer is observed to be approximately 5 μm thick. In a long-term test of the glucose oxidase activity, the glucose oxidase/albumin layer is observed to be appreciably more stable than the glucose oxidase only layer formed in Example 1.

EXAMPLE 3

A 2.4 mg/mL solution of rabbit anti-fluorescein antibody (affinity purified) is prepared utilizing a borate buffer solution (pH 9.0) as the solvent. The pH value was selected to retain maximum antibody binding activity. An electrodeposition cell is filled with this solution and the biosensor electrode on which the antibody is to be deposited, along with a counter electrode, are submerged inside the cell. Electrical connections are made to a galvanostat and the current is maintained at a constant density of 5 mA/cm$^2$ on the electrode surface. The current flow is oriented in a direction that results in a negative net charge on the biosensor electrode surface to attract the positively charged antibody molecules. The current is applied for 50 minutes. The electrode was removed from the antibody solution and submerged in deionized, distilled water with no agitation for 5 seconds to remove residual antibody.

The electrode was then submerged in a solution containing 2.5% by volume glutaraldehyde in phosphate buffered saline (pH 7.4) for 30 minutes to covalently crosslink the antibody molecules together and form a water-insoluble mass. The electrode is again submerged in deionized, distilled water for 5 seconds and allowed to dry in air for 30 minutes. Inspection of the electrode reveals that the electrodeposited antibody layer is approximately 5.5 μm thick when dry.

Although the invention has been described in detail with reference to certain preferred embodiments and specific examples, variations and modifications exist within the scope and spirit of the invention as described and as defined in the following claims.

What is claimed is:

1. A method of preparing a biosensor electrode having a biomolecular component comprising
   preparing a solution of at least one species of biomolecule intended for deposition buffered range sufficient to prevent denaturation of the biomolecules, and to a pH such that all species of biomolecules intended for deposition have the same net electric charge sign due to their respective isoelectric points,
   immersing said biosensor electrode and a counter electrode in the solution,
   applying a variable potential of less than 1 volt across the biosensor electrode and counter electrode, with the potential varying in a manner selected to provide a substantially constant electric current between the electrodes sufficient to cause migration of the biomolecules intended for deposition to said biosensor electrode and accumulation thereon.

2. The method of claim 1 further comprising the step maintaining the substantially constant electric current between the electrodes for a time sufficient to allow accumulation on the biosensor electrode of a film of biomolecules having an average film thickness between 1.0 to 10 micrometers.

3. The method of claim 2 further comprising the step of introducing the biosensor electrode and accumulated deposition into a solution of a crosslinking agent present in an amount and for sufficient time to crosslink the biomolecules together to form a water-insoluble mass on the biosensor electrode.

4. The method of claim 1 wherein the preparation step includes preparation of a solution containing a protein to be deposited.

5. The method of claim 4 wherein the protein is an enzyme.

6. The method of claim 4 wherein the protein is an antibody.

7. A method of preparing a biosensor electrode having a proteinaceous component comprising
   preparing a solution of at least one species of protein intended for deposition buffered sufficient to prevent denaturation of the protein
   immersing said biosensor electrode and a counter electrode in the solution,
   applying a variable potential of less than 1 volt across the biosensor electrode and counter electrode, with the potential varying with time in a manner selected to provide a substantially constant electric current between the electrodes sufficient to cause migration of the biomolecules intended for deposition to said biosensor electrode and accumulation thereon, and
   crosslinking said deposited accumulation on the biosensor electrode with a crosslinking agent to form a water-insoluble mass on the biosensor electrode.

8. A method of preparing an enzymatic biosensor comprising
   preparing a solution of glucose oxidase intended for deposition on a biosensor electrode,
   immersing said biosensor electrode and a counter electrode in the solution,
   applying a variable potential of less than 1 volt across the biosensor electrode and counter electrode, with the potential varying with time in a manner selected to provide a substantially constant electric current between the electrodes sufficient to cause migration of the glucose oxidase intended for deposition to said biosensor electrode and accumulation of a film less than 10 micrometers thereon.

* * * * *